United States Patent
Stelling et al.

(10) Patent No.: US 11,536,709 B2
(45) Date of Patent: Dec. 27, 2022

(54) SYSTEMS, METHODS, AND APPARATUS FOR PROCESSING, ORGANIZING, AND DISPLAYING PLATELET CELL DATA

(71) Applicant: Siemens Healthcare Diagnostics, Inc., Tarrytown, NY (US)

(72) Inventors: Frederick Stelling, Newburgh, NY (US); Val Jones, Malahide Dublin (IE); William Canfield, Croton on Hudson, NY (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1126 days.

(21) Appl. No.: 16/090,190

(22) PCT Filed: Mar. 30, 2016

(86) PCT No.: PCT/US2016/025102
§ 371 (c)(1),
(2) Date: Sep. 28, 2018

(87) PCT Pub. No.: WO2017/171762
PCT Pub. Date: Oct. 5, 2017

(65) Prior Publication Data
US 2019/0113432 A1    Apr. 18, 2019

(51) Int. Cl.
*G01N 33/49* (2006.01)
*G01N 35/00* (2006.01)
(Continued)

(52) U.S. Cl.
CPC .............. *G01N 33/49* (2013.01); *G01N 15/14* (2013.01); *G01N 35/00722* (2013.01);
(Continued)

(58) Field of Classification Search
CPC ........ G16H 10/40; G16H 50/20; G01N 15/14; G01N 33/49; G01N 35/00722;
(Continued)

(56) References Cited

U.S. PATENT DOCUMENTS 5,812,419 A * 9/1998 Chupp ............... G01N 35/1004
702/20
6,524,858 B1 * 2/2003 Zelmanovic ........... G01N 15/14
436/166
(Continued)

FOREIGN PATENT DOCUMENTS

CN    101206218    6/2008
CN    103592429    2/2014
(Continued)

OTHER PUBLICATIONS

Tocchetti E.V. et al., "Assessment of In Vitro-Generated Platelet Microparticles Using a Modified Flow Cytometric Strategy"; Thrombosis Research, Tarrytown, NY, US. vol. 103, No. 1; pp. 47-55; 2001.
(Continued)

*Primary Examiner* — Michael P LaPage
(74) *Attorney, Agent, or Firm* — Dugan & Dugan, PC

(57) ABSTRACT

Platelet cell data may be obtained from analysis of a blood sample by a hematology analyzer or like device. Systems and apparatus may process the platelet cell data in accordance with platelet parameter thresholds selected by a user. The platelet cell data may then be categorized and displayed in one or more useful forms for medical diagnostic and/or research purposes. The platelet cell data may be categorized and displayed in, e.g., tabular and/or graphical form based on the user-selected platelet parameter thresholds. Methods of processing platelet cell data for categorizing and display-
(Continued)

ing the platelet cell data in one or more useful forms are also provided, as are other aspects.

20 Claims, 6 Drawing Sheets

(51) Int. Cl.
*G16H 50/20* (2018.01)
*G16H 10/40* (2018.01)
*G16B 50/30* (2019.01)
*G16B 40/20* (2019.01)
*G01N 15/14* (2006.01)
*G01N 15/00* (2006.01)

(52) U.S. Cl.
CPC .............. *G16B 40/20* (2019.02); *G16B 50/30* (2019.02); *G16H 10/40* (2018.01); *G16H 50/20* (2018.01); *G01N 2015/0084* (2013.01); *G01N 2035/00891* (2013.01)

(58) Field of Classification Search
CPC . G01N 2015/0084; G01N 2035/00891; G16B 40/20; G16B 50/30
See application file for complete search history.

(56) References Cited

U.S. PATENT DOCUMENTS

| 8,017,078 | B2 | 9/2011 | Linssen et al. |
| 9,176,112 | B2 | 11/2015 | Zhang et al. |
| 2003/0175831 | A1* | 9/2003 | Canton ............ G01N 33/56966 435/287.2 |
| 2006/0004541 | A1 | 1/2006 | Miyamoto |
| 2007/0247463 | A1 | 10/2007 | Qian et al. |
| 2014/0149938 | A1 | 5/2014 | Nishimori et al. |
| 2017/0074863 | A1* | 3/2017 | Masuda ................. G01N 1/38 |
| 2018/0080760 | A1* | 3/2018 | Allier ................. G01N 21/4788 |
| 2018/0202903 | A1* | 7/2018 | Chou ..................... G01N 21/76 |
| 2021/0296570 | A1* | 9/2021 | Wang ..................... H01L 43/08 |

FOREIGN PATENT DOCUMENTS

| CN | 103852404 | 6/2014 |
| CN | 104755905 A | 7/2015 |
| CN | 104903699 | 9/2015 |
| WO | WO2014106132 | 7/2014 |

OTHER PUBLICATIONS

Martinez W. et al., "Computational Statistics Handbook with MATLAB (2nd edition)," Computational Statistic Handbook with MATLAB (2nd edition), CRC Press;; pp. 149-155, 2007.
Michelson A.D., "Platelets (Third Edition)," Academic Press; p. 551, 2013.
International Search Report and Written Opinion of International Application No. PCT/US2016/025102 (SAG-029-WO) dated Jun. 10, 2016.
Chinese Search Report of Chinese Application No. 201680078378 dated Mar. 23, 2021.
Tocchetti, E.V. et al.: "Assessment of In Vitro-Generated Platelet Microparticles Using a Modified Flow Cytometric Strategy"; Thrombosis Research; Tarrytown; NY, US. vol. 103, No. 1; pp. 47-55; XP001023450; ISSN: 0049-3848; DOI: 10.1016/S0049-3848(01)00263-8; 2001.
Martinez, W. et al.: "Computational Statistics Handbook with MATLAB (2nd edition)"; in: "Computational Statistic Handbook with MATLAB (2nd edition)"; CRC Press; P055276131; ISBN: 978-1-4200-1086-2; pp. 149-155; 2007.
Michelson, A.D. : "Platelets (Third Edition)"; Academic Press; XP055276138; ISBN: 978-0-12-387837-3; pp. 551-551; 2013.
Chinese Search Report of Chinese Application No. 201680078378 dated Jun. 21, 2019.

* cited by examiner

500

```
THRESHOLD CONFIGURATION
```

┌─ 524 ─────────────────────┬─ 525 ─────────────────────┐
| FIRST PARAMETER  530  533 | SECOND PARAMETER  537  540 |
|                 LOW  HIGH |                  LOW  HIGH |
| (Range A1 - A2) Edit Edit | (Range B1 - B2) Edit  Edit |
|       ↑          ↑   ↑    |       ↑          ↑    ↑   |
|      528        529 531 532 534  535   536  538 539 541|

526 — RESTORE DEFAULTS      527 — SAVE

| 645 ↓ | PLATELET ANALYSIS RESULTS | | 646 |
|---|---|---|---|
|  | 2P < LTh | LTh ≤ 2P ≤ HTh | 2P > HTh |
| 1P > HTh | 35 | 98 | 7 |
|  | 2.5% | 7.0% | 0.5% |
| LTh ≤ 1P ≤ HTh | 182 | 671 | 126 |
|  | 13.0% | 48.0% | 9.0% |
| 1P < LTh | 28 | 217 | 35 |
|  | 2.0% | 15.5% | 2.5% |

SYSTEMS, METHODS, AND APPARATUS FOR PROCESSING, ORGANIZING, AND DISPLAYING PLATELET CELL DATA

CROSS REFERENCE TO RELATED APPLICATION

This is a 371 of PCT/US2016/025102, filed Mar. 30, 2016, the disclosure of which is hereby incorporated by reference herein in its entirety for all purposes.

FIELD

The invention relates generally to medical diagnostics and, more particularly, to automated systems, methods, and apparatus for processing platelet cell data obtained from analysis of a blood sample.

BACKGROUND

A hematology analyzer may be used to automatically analyze large numbers of blood samples. The blood samples may have been taken from humans, lab animals (e.g., rats, mice, etc.), and/or other mammals (e.g., horses, cattle, etc.). The analysis of the blood samples may include determination of one or more parameters related to one or more blood components, such as, e.g., red blood cells, white blood cells, and/or platelets. Parameters related to platelets may include the number of platelet cells found in a blood sample, the volume of each cell, and the refractive index of each cell. The refractive index of a platelet cell is a ratio of the speed of light in a vacuum to the speed of light in the platelet cell. A hematology analyzer may collect and store platelet cell data in a memory device of the hematology analyzer (or in a memory device of another system or computer coupled to the hematology analyzer). The platelet cell data may be in the form of a data list (or other similar data file or structure). The data list may identify individual platelet cells and their respective volume and refractive index values. The platelet cell data in such a form, however, may not be readily useful for medical diagnostic and/or research purposes.

Accordingly, there is a need for systems, methods, and apparatus for processing platelet cell data into one or more useful forms.

SUMMARY

According to one aspect, a method of processing platelet cell data stored in a memory device is provided. The method includes receiving first and second threshold values for a first parameter and third and fourth threshold values for a second parameter; establishing first high, first normal, and first low ranges for the first parameter and second high, second normal, and second low ranges for the second parameter in response to receiving the first, second, third, and fourth threshold values; establishing a plurality of categories, each category based on a combination of one of the first high, first normal, and first low ranges with one of the second high, second normal, and second low ranges; retrieving the platelet cell data from the memory device, the platelet cell data indicating a plurality of platelet cells comprising a respective plurality of first parameter values and a corresponding plurality of second parameter values, wherein each platelet cell of the plurality of platelet cells corresponds to a respective first parameter value and a respective second parameter value; determining for each first parameter value and each corresponding second parameter value whether the first parameter value is in the first high, first normal, or first low range and whether the corresponding second parameter value is in the second high, second normal, or second low range; and computing a number of the plurality of platelet cells in each of the plurality of categories in response to the determining.

According to another aspect, apparatus for processing platelet cell data is provided. The apparatus includes a user interface and a processor coupled to the user interface. The user interface comprises a user input device and a display device. The processor is configured to: receive via the user interface first and second threshold values for a first parameter and third and fourth threshold values for a second parameter; establish first high, first normal, and first low ranges for the first parameter and second high, second normal, and second low ranges for the second parameter in response to receiving the first, second, third, and fourth threshold values; establish a plurality of categories, each category based on a combination of one of the first high, first normal, and first low ranges with one of the second high, second normal, and second low ranges; retrieve the platelet cell data, the platelet cell data indicating a plurality of platelet cells comprising a respective plurality of first parameter values and a corresponding plurality of second parameter values, wherein each platelet cell of the plurality of platelet cells corresponds to a respective first parameter value and a respective second parameter value; determine for each first parameter value and each corresponding second parameter value whether the first parameter value is in the first high, first normal, or first low range and whether the corresponding second parameter value is in the second high, second normal, or second low range; and compute a number of the plurality of platelet cells in each of the plurality of categories in response to the determining.

Still other aspects, features, and advantages of the invention may be readily apparent from the following detailed description wherein a number of example embodiments and implementations are described and illustrated, including the best mode contemplated for carrying out the invention. The invention may also include other and different embodiments, and its several details may be modified in various respects, all without departing from the scope of the invention. Accordingly, the drawings and descriptions are to be regarded as illustrative in nature, and not as restrictive. The invention covers all modifications, equivalents, and alternatives of the aspects disclosed herein.

BRIEF DESCRIPTION OF THE DRAWINGS

Persons skilled in the art will understand that the drawings, described below, are for illustrative purposes only. The drawings are not necessarily drawn to scale and are not intended to limit the scope of this disclosure in any way.

FIG. 5 illustrates an example of an input screen according to embodiments.

FIG. 6 illustrates an example of a table showing results of processed platelet cell data according to embodiments.

DETAILED DESCRIPTION

Reference will now be made in detail to the example embodiments of this disclosure, which are illustrated in the accompanying drawings. Wherever possible, the same reference numbers will be used throughout the drawings to refer to the same or like parts.

The aforementioned problem of having platelet cell data in a form that may not be readily useful for medical diagnostic and/or research purposes may be overcome by one or more embodiments of the invention. In one aspect, a system for processing platelet cell data may include a hematology analyzer configured to analyze samples of blood and to create platelet cell data based on the analysis of the samples of blood. The hematology analyzer may include a memory device for storing the created platelet cell data. The system may also include apparatus coupled to the hematology analyzer and, more particularly, to the memory device. The apparatus may be a computer or like device having suitable data processing capabilities and programming. The apparatus may include a user interface and a processor, among other components, and may be configured to retrieve the platelet cell data from the memory device and to process that data into one or more useful forms based on user-selected thresholds. The one or more useful forms may include a table having a tic-tac-toe arrangement, wherein each platelet cell identified in the platelet cell data may be processed into one of nine categories based on one or more of the user-selected thresholds. The table may indicate, e.g., the count and/or percentage of platelet cells in each of the nine categories. The one or more useful forms of processed platelet cell data may also include graphical forms, such as, e.g., cytograms and histograms, each graphically illustrating one or more of the results of the processed platelet cell data. Each table, cytogram, and/or histogram may be displayed on a display device of the apparatus. The results of the processed platelet cell data may also be included in a data export file for transfer to other systems and/or devices. In other aspects, methods of processing platelet cell data are also provided, as will be explained in greater detail below in connection with FIGS. 1-9.

Figures 1, 2:
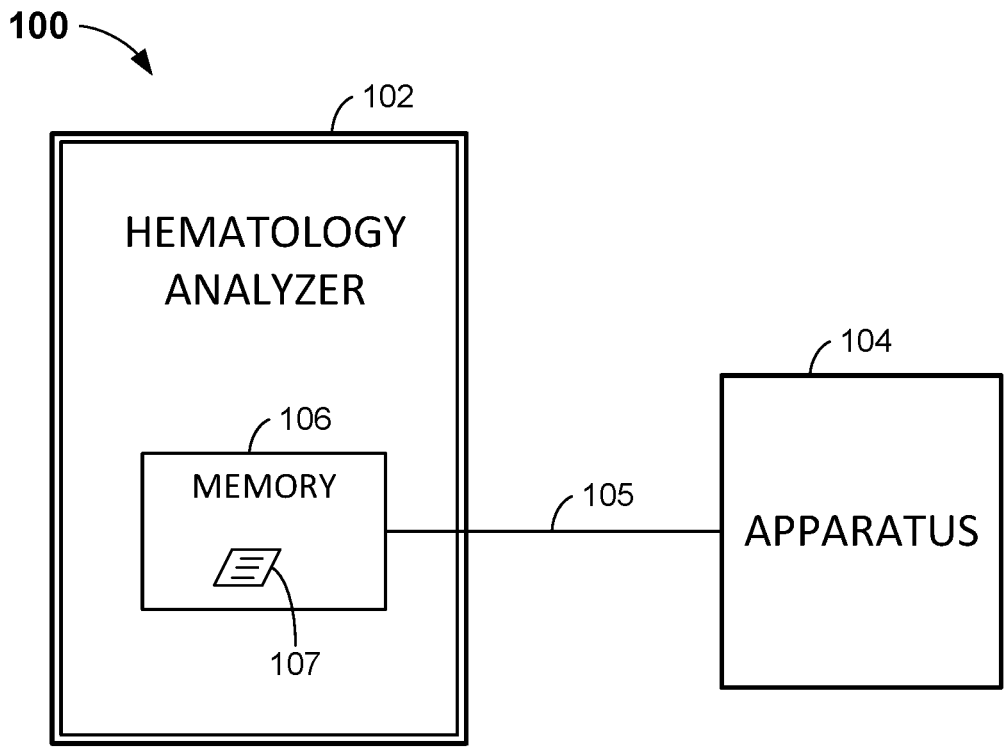
FIG. 1 illustrates a block diagram of a system for processing platelet cell data according to embodiments.
FIG. 2 illustrates an example of platelet cell data stored in the system of FIG. 1.

FIG. 1 illustrates a system 100 for processing platelet cell data in accordance with one or more embodiments. System 100 may include a hematology analyzer 102 and apparatus 104 coupled to hematology analyzer 102 via a wired connection 105. In other embodiments, apparatus 104 may be coupled to hematology analyzer 102 via a wireless connection. Hematology analyzer 102 may include a memory device 106, which may be, e.g., a RAM (random access memory), a WORM (write once, read many), a hard disk, a removable disk, or like device. Hematology analyzer 102 may include other components (not shown) including, e.g., a processor, a portable storage drive, a display device, and a keyboard or other user input device. Hematology analyzer 102 may be configured to automatically analyze large numbers of blood samples to determine one or more parameters related to one or more blood components, such as, e.g., red blood cells, white blood cells, and/or platelets. Parameters related to platelets may include the number of platelet cells found in each blood sample, the volume of each platelet cell, and the refractive index of each platelet cell. Hematology analyzer 102 may further include appropriate software programs executable on its processor and stored in memory device 106 for performing the automatic analysis of blood samples. Hematology analyzer 102 may be, e.g., an ADVIA 2120i Hematology System, by Siemens Healthcare GmbH, of Munich, Germany.

The data collected by hematology analyzer 102, including platelet cell data 107, may be stored in memory device 106. Alternatively, the data collected by hematology analyzer 102 may be stored in other devices or systems coupled to hematology analyzer 102. The platelet cell data may be in the form of a data list (or other similar data file or structure). The data list may identify individual platelet cells and their respective volume and refractive index values, as shown in the example of platelet cell data in FIG. 2.

FIG. 2 illustrates platelet cell data 207 that may be stored in system 100 in accordance with one or more embodiments. As shown, platelet cell data 207 may list each platelet cell in a respective row along with its corresponding values of volume and refractive index (RI), as identified and determined by hematology analyzer 102. Volume values may be given in units of femtoliters (fL), while refractive index values may be given in units of RI (which is actually dimensionless, because refractive index is a ratio). In some embodiments, platelet cell data 207 may list 5,000 to 6,000 platelet cells per blood sample. In some embodiments, platelet cell data 207 may list the results from a single blood sample. In other embodiments, platelet cell data 207 may list the results from a plurality of blood samples, wherein results for each blood sample are separately identified.

Apparatus 104 may be a stand-alone computer, workstation, or other data processing device. In some embodiments, apparatus 104 may be a personal or laptop computer. Apparatus 104 is configured to process platelet cell data 107 or 207 into one or more forms that may be more useful for medical diagnostic and/or research purposes than the form of, e.g., platelet cell data 207. In particular, apparatus 104 is configured to retrieve platelet cell data 107 or 207 from memory device 106 (or, alternatively, from wherever stored). Apparatus 104 is also configured to categorize and display on a display device the platelet cell data in one or more tabular or graphical forms as described below in connection with FIGS. 4-9. An embodiment of apparatus 104 is shown in FIG. 3.

Figure 3:
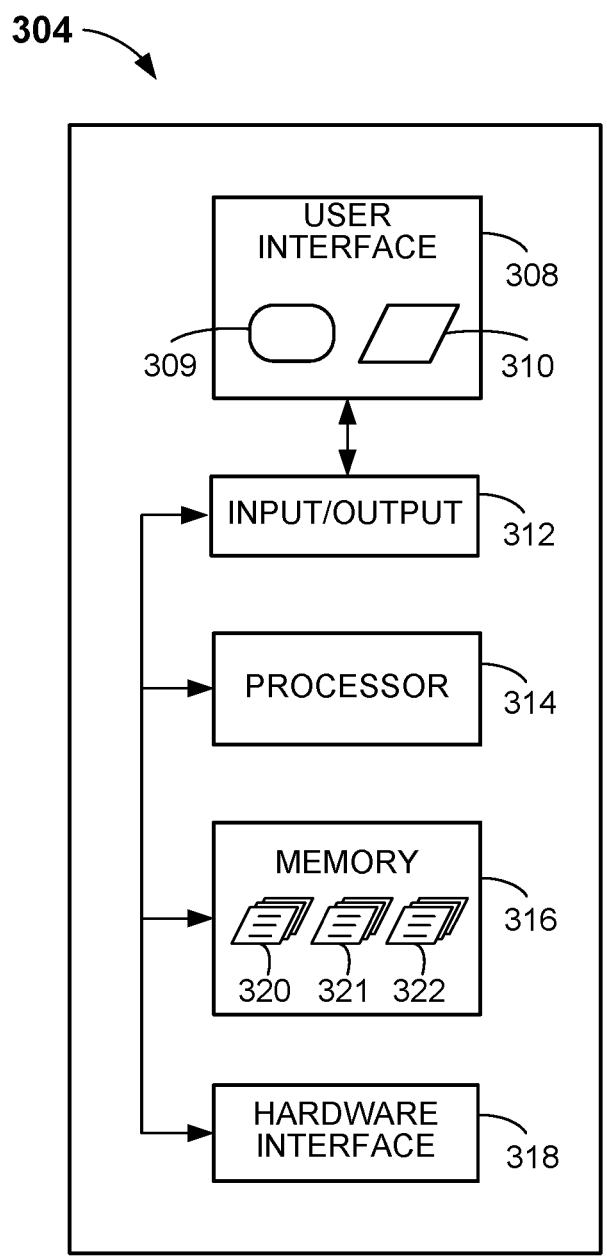
FIG. 3 illustrates a block diagram of apparatus for processing platelet cell data according to embodiments.

FIG. 3 illustrates apparatus 304 that may be used in system 100 in accordance with one or more embodiments. Apparatus 304 may be any suitable general purpose or special purpose computer or like device capable of performing the functions described herein. Apparatus 304 may be, e.g., a workstation, a personal computer, or a laptop computer and may be a standalone device. Apparatus 304 may include any suitable components such as one or more of the following: a user interface 308, input/output device drivers 312 (which include a graphics display driver), a processor 314 (which may be, e.g., a microprocessor, central processing unit, digital signal processor, controller, etc.), a memory device 316 (which may include one or more RAMs, ROMs (read only memory), hard disks, optical or magnetic disks, removable disks, etc.), and a hardware interface 318. User interface 308 may include, e.g., a display device 309 and one or more user input devices 310 such as, e.g., a keyboard, mouse, touch pad, etc. Display device 309 is capable of displaying various graphics. Processor 314 may execute software programs/programming instructions that may be stored in memory device 316 to perform, for example, the functions of method 400 described below. Memory device 316 may be suitable for storing, e.g., operating system software/device drivers 320, user software programs 321, and data 322. Hardware interface 318 may establish direct communication with other devices, servers/computers, and/or peripherals (such as, e.g., hematology analyzer 102) and/or may establish communication with the Internet and/or any other suitable communications networks. Apparatus 304 may additionally or alternatively include other suitable components.

Figure 4:
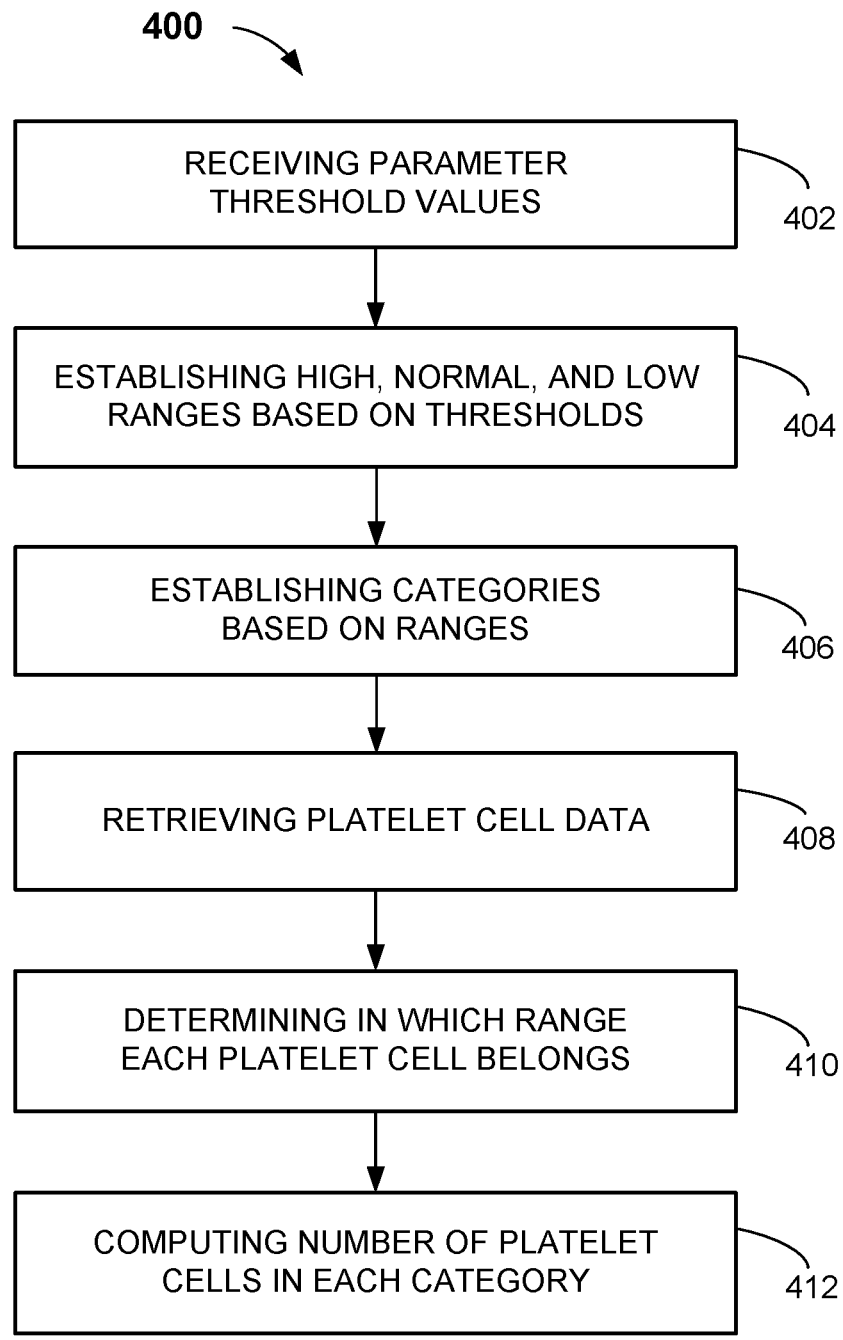
FIG. 4 illustrates a flowchart of a method of processing platelet cell data according to embodiments.

FIG. 4 illustrates a flowchart of a method 400 of processing platelet cell data in accordance with one or more embodiments. Method 400 may include at process block 402 receiving parameter threshold values. In some embodiments, apparatus 304 may receive one or more parameter threshold values from a user entering the parameter threshold values via user interface 308 as described below in connection with FIG. 5. The parameter threshold values may be related to a first parameter and a second parameter. In some embodiments, the first parameter may be platelet cell volume, and the second parameter may be platelet cell refractive index. The first parameter may have first and second threshold values, which may be, e.g., a high platelet volume threshold value and a low platelet volume threshold value, respectively. The second parameter may have third and fourth threshold values, which may be, e.g., a high platelet refractive index threshold value and a low platelet refractive index threshold value, respectively. Alternative embodiments may have parameter threshold values other than high and low values, and the threshold values may be related to one or more other platelet cell parameters.

FIG. 5 illustrates a threshold configuration input screen 500 wherein a user can enter desired platelet threshold values for a first and/or a second platelet cell parameter in accordance with one or more embodiments. Input screen 500 may be displayed on a suitable display device, such as, e.g., display device 309 of apparatus 304. Input screen 500 may include a first parameter region 524 and a second parameter region 525. Other embodiments of input screen 500 may have more or less parameter regions.

First parameter region 524 may indicate a range 528 of a predetermined minimum value A1 and a predetermined maximum value A2 related to the first parameter. For example, if the first parameter is platelet cell volume, the minimum value A1 may be 0 fL and the maximum value A2 may be 60 fL. Accordingly, range 528 may appear in first parameter region 524 as "RANGE 0 fL-60 fL." Other values may be used. First parameter region 524 may include a LOW threshold value field 529 having a corresponding up arrow button 530 and a corresponding down arrow button 531. The up arrow button 530 allows a user to increase a threshold value in field 529, while the down arrow button 531 allows the user to decrease a threshold value in field 529. First parameter region 524 may also include a HIGH threshold value field 532 having a corresponding up arrow button 533 and a corresponding down arrow button 534. The up arrow button 533 allows a user to increase a threshold value in field 532, while the down arrow button 534 allows the user to decrease a threshold value in field 532.

Second parameter region 525 may indicate a range 535 of a predetermined minimum value B1 and a predetermined maximum value B2 related to the second parameter. For example, if the second parameter is platelet cell refractive index, the minimum value B1 may be 1.35 RI and the maximum value B2 may be 1.40 RI. Accordingly, range 535 may appear in second parameter region 525 as "RANGE 1.35 RI-1.40 RI." Other values may be used. Second parameter region 525 may include a LOW threshold value field 536 having a corresponding up arrow button 537 and a corresponding down arrow button 538. The up arrow button 537 allows a user to increase a threshold value in field 536, while the down arrow button 538 allows the user to decrease a threshold value in field 536. Second parameter region 525 may also include a HIGH threshold value field 539 having a corresponding up arrow button 540 and a corresponding down arrow button 541. The up arrow button 540 allows a user to increase a threshold value in field 539, while the down arrow button 541 allows the user to decrease a threshold value in field 539.

Input screen 500 may also include a RESTORE DEFAULTS button 526 and a SAVE button 527. The RESTORE DEFAULTS button 526 when activated allows a user to set threshold value fields 529, 532, 536, and 539 to predetermined default threshold values. The SAVE button 527 when activated allows a user to save the threshold values appearing in threshold value fields 529, 532, 536, and 539. The saved threshold values may be stored in, e.g., memory device 316 of apparatus 304. Some embodiments of input screen 500 may have additional buttons such as, e.g., a PRINT REPORT button and/or a HELP button.

Some embodiments of input screen 500 may have additional input fields, such as, e.g., a species input field. A drop-down menu may be associated with the species input field and may include, e.g., the selectable values of "human," "rodent," and/or "other mammal." Accordingly, in those embodiments, the predetermined minimum values A1 and B1, the predetermined maximum values A2 and B2, and the default threshold values invoked via the RESTORE DEFAULTS button 526 may correspond to the particular species selected in the species input field.

In some embodiments, method 400 may be part of software that is executed in a hematology analyzer. In those embodiments, alternative versions of input screen 500 may include additional regions and/or input fields for entering additional information and/or thresholds related to one or more other analyses of blood components in addition to platelets.

Returning to FIG. 4, method 400 may include at process block 404 establishing high, normal, and low ranges based on the received threshold values. For example, assume the following: the first parameter is platelet cell volume, the predetermined minimum value is 0 fL, the maximum predetermined value is 60 fL, the user-selected LOW threshold value is, e.g., 7 fL, and the user-selected HIGH threshold value is, e.g., 20 fL. Processor 314 (executing method 400) may then establish a high range of greater than 20 fL to 60 fL, a normal range of greater than or equal to 7 fL to 20 fL, and a low range of from 0 fL to less than 7 fL. Other ranges and boundary conditions (i.e., whether values equal to the threshold value are included in a range) are possible.

Similarly, for the second parameter, assume the following: the second parameter is platelet cell refractive index, the predetermined minimum value is 1.35 RI, the maximum predetermined value is 1.40 RI, the user-selected LOW threshold value is, e.g., 1.365 RI, and the user-selected HIGH threshold value is, e.g., 1.395 RI. Processor 314 (executing method 400) may then establish a high range of greater than 1.395 RI to 1.4 RI, a normal range of greater than or equal to 1.365 RI to 1.395 RI, and a low range of from 1.35 RI to less than 1.365 RI. Other ranges and boundary conditions are possible.

Method 400 may include at process block 406 establishing categories based on the high, normal, and low ranges established at process block 404. Categories may be established based on combinations of one of the high, normal, and low ranges of the first parameter with one of the high, normal, and low ranges of the second parameter. In those embodiments wherein each possible combination of first and second parameter ranges is desired, processor 314 (executing method 400) may establish nine categories as follows:

1) first parameter high range with second parameter low range (e.g., platelet cell high volume range with platelet cell low refractive index range);

2) first parameter high range with second parameter normal range (e.g., platelet cell high volume range with platelet cell normal refractive index range);

3) first parameter high range with second parameter high range (e.g., platelet cell high volume range with platelet cell high refractive index range);

4) first parameter normal range with second parameter low range (e.g., platelet cell normal volume range with platelet cell low refractive index range);

5) first parameter normal range with second parameter normal range (e.g., platelet cell normal volume range with platelet cell normal refractive index range);

6) first parameter normal range with second parameter high range (e.g., platelet cell normal volume range with platelet cell high refractive index range);

7) first parameter low range with second parameter low range (e.g., platelet cell low volume range with platelet cell low refractive index range);

8) first parameter low range with second parameter normal range (e.g., platelet cell low volume range with platelet cell normal refractive index range); and 9) first parameter low range with second parameter high range (e.g., platelet cell low volume range with platelet cell high refractive index range).

In other embodiments, less than nine categories may be established.

At process block 408, method 400 may include retrieving platelet cell data created by a hematology analyzer such as, e.g., hematology analyzer 102. As described above, platelet cell data may be stored in memory device 106 of hematology analyzer 102. In response to user-execution of method 400 in apparatus 104 or 304, platelet cell data 107 or 207 may be retrieved by apparatus 104 or 304 via wired connection 105 (or alternatively via a wireless connection) and hardware interface 318 (which may include, e.g., a USB (Universal Serial Bus) port). Alternatively, the platelet cell data may be retrieved from a portable storage device coupled directly to apparatus 104 or 304 at hardware interface 318. The retrieved platelet cell data may be stored, e.g., in memory device 316 or in another suitable location within apparatus 304 (e.g., a suitable local cache or buffer).

In some embodiments, the platelet cell data may not include refractive index values for large platelet cells, but instead may include values for hemoglobin concentration in units of grams/deciliter (g/dL). In these cases, method 400 may convert the hemoglobin concentration (HC) values to refractive index (RI) values via the equation: RI=HC× 0.001942+1.345.

At process block 410, method 400 may include determining in which of the high, normal, and low ranges each of the platelet cells belongs. Processor 314 includes appropriate logic circuitry to perform arithmetic comparisons of the platelet cell data with the received user-thresholds. For example, referring to FIG. 2 and continuing with the above example wherein the first parameter is platelet cell volume and the second parameter is platelet cell refractive index, processor 314 may arithmetically compare Cell 1's volume value of 27 fL to a user-selected LOW threshold value of, e.g., 7 fL and a user-selected HIGH threshold value of, e.g., 20 fL. As a result of those arithmetic comparisons, processor 314 may determine that Cell 1 belongs in the high volume range. Similarly, processor 314 may arithmetically compare Cell 1's refractive index value of 1.365 RI to a user-selected LOW threshold value of, e.g., 1.365 RI and a user-selected HIGH threshold value of, e.g., 1.395 RI. As a result of those arithmetic comparisons, processor 314 may determine that Cell 1 belongs in the normal refractive index range. Processor 314 may continue such determinations for each platelet cell in the retrieved platelet cell data on, e.g., a per blood sample basis and store the results in memory device 316.

At process block 412, method 400 may include computing the number of platelet cells in each category based on the results determined at process block 410. For example, continuing with the above example, in response to determining that Cell 1's volume value belongs in the high volume range and that Cell 1's refractive index value belongs in the normal refractive index range, processor 314 may determine that Cell 1 belongs in category 2 (above) and may then accordingly increment a counter for category 2 by one. Each of the nine categories may have a dedicated counter in apparatus 304 controlled by processor 314. In some embodiments, each of the counters may be reset to zero for platelet cell data corresponding to a new blood sample. The number of platelet cells belonging in each category may be computed alternatively in any suitable manner.

In some embodiments, method 400 may also include displaying a table on a display device of the number of platelet cells in each of the established categories. The table may be displayed on, e.g., display device 309 of apparatus 304. For embodiments with the nine established categories described above, the table may have a tic-tac-toe arrangement, wherein the nine categories are arranged in three rows by three columns. The three rows may correspond to the high, normal, and low ranges, respectively, of the first parameter (e.g., platelet cell volume), and the three columns may correspond to the high, normal, and low ranges, respectively, of the second parameter (e.g., platelet cell refractive index). An example of such a table is described below in connection with FIG. 6.

In some embodiments, method 400 may further include computing a percentage of the number of platelet cells in each of the established categories, and displaying in a table on a suitable display device, such as, e.g., display device 309, the computed percentages of platelet cells in each of the established categories. Processor 314 may compute the percentages by taking the number of cells computed above in process block 412 for each established category and dividing by the total number of platelet cells identified for a given blood sample (or sample size) and multiplying by 100. For embodiments with the nine established categories described above, the table may have a tic-tac-toe arrangement, wherein the nine categories are arranged in three rows by three columns. The three rows may correspond to the high, normal, and low ranges, respectively, of the first parameter (e.g., platelet cell volume), and the three columns may correspond to the high, normal, and low ranges, respectively, of the second parameter (e.g., platelet cell refractive index). In some embodiments, the table may be the same as the table described above for displaying the number of platelet cells in each of the established categories.

FIG. 6 illustrates an example of a platelet analysis results table 600 in accordance with one or more embodiments. Table 600 displays platelet analysis results for nine established categories and may have a tic-tac-toe arrangement. That is, table 600 may have the nine categories arranged in three double-lined rows by three columns. Table 600 may have a header column 645 with three row labels (1P>HTh, LTh≤1P≤HTh, and 1P<LTh). The three row labels represent the respective high, normal, and low ranges of the first parameter as established in process block 404, which are based on the user-selected first parameter threshold values received in process block 402. Table 600 may also have a header row 646 with three column labels (2P<LTh, LTh≤2P≤HTh, and 2P>HTh). The three column labels represent the respective low, normal, and high ranges of the second parameter as established in process block 404, which are based on the user-selected second parameter threshold values received in process block 402.

Table 600 further has a category results area 647, wherein categories 1-9 described above are arranged as follows: category 1 is in the row labeled 1P>HTh (first parameter high range) and column labeled 2P<LTh (second parameter low range); category 2 is in the row labeled 1P>HTh and column labeled LTh≤2P≤HTh (second parameter normal range); category 3 is in the row labeled 1P>HTh and column labeled 2P>HTh (second parameter high range); category 4 is in the row labeled LTh≤1P≤HTh (first parameter normal range) and column labeled 2P<LTh; category 5 is in the row labeled LTh≤1P≤HTh and column labeled LTh≤2P≤HTh; category 6 is in the row labeled LTh≤1P≤HTh and column labeled 2P>HTh; category 7 is in the row labeled 1P<LTh (first parameter low range) and column labeled 2P<LTh; category 8 is in the row labeled 1P<LTh and column labeled LTh≤2P≤HTh; and category 9 is in the row labeled 1P<LTh and column labeled 2P>HTh. The arrangement of categories in category results area 647 may be different in other embodiments.

In some embodiments, category results area 647 shows both the number of platelet cells and the percentage of platelet cells in each category, as shown in FIG. 6. For example, continuing with the above example wherein the first parameter is platelet cell volume and the second parameter is platelet cell refractive index, the results 648 for category 9 (i.e., low volume range and high refractive index range) are 35 platelet cells representing 2.5% of all platelet cells identified in the one or more blood samples represented by table 600.

Method 400 may also include in some embodiments displaying graphically on a display device, such as, e.g., display device 309 of apparatus 304, the number of platelet cells in each of the established categories. In some embodiments, the graphical display may be a cytogram. A cytogram as described herein may graphically illustrate differences in the distribution of platelet cells within a blood sample (or group of blood samples) based on, e.g., first and second parameters.

Figure 7:
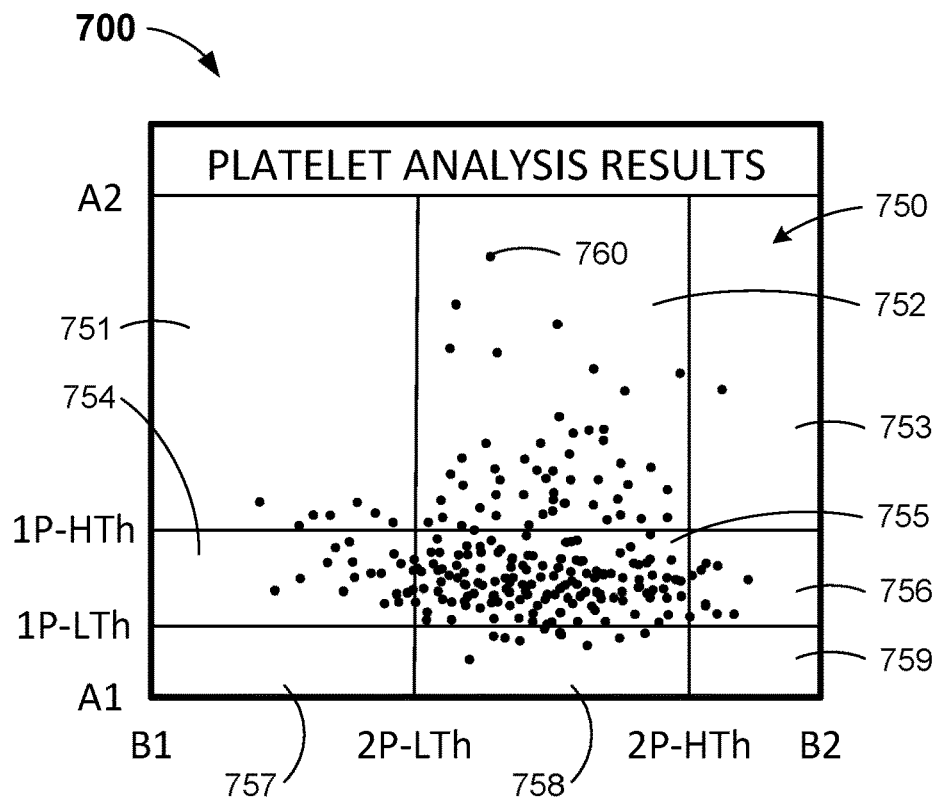
FIG. 7 illustrates an example of a cytogram showing results of processed platelet cell data according to embodiments.

FIG. 7 an example of a cytogram showing results of processed platelet cell data according to embodiments. Cytogram 700 graphically shows the distribution of platelet cells based on the high and low first parameter thresholds and the high and low second parameter thresholds received at process block 402. Cytogram 700 may be arranged with the first parameter scaled on the vertical axis, extending from the predetermined minimum value A1 to the predetermined maximum value A2. For example, continuing with the above example wherein the first parameter is platelet cell volume, the scale of the vertical axis may be 0 fL to 60 fL.

The user-selected low and high threshold values for the first parameter (labeled "1P-LTh" and "1P-HTh," respectively) are indicated with horizontal lines as shown. The second parameter may be scaled on the horizontal axis, extending from the predetermined minimum value B1 to the predetermined maximum value B2. For example, continuing again with the above example wherein the second first parameter is platelet cell refractive index, the scale of the vertical axis may be 1.35 RI to 1.40 RI. The user-selected low and high threshold values for the second parameter (labeled "2P-LTh" and "2P-HTh," respectively) are indicated with vertical lines as shown.

The resulting cytogram display area 750 accordingly displays the nine categories established at process block 406. In particular, category 1 is represented in a display area 751, category 2 is represented in a display area 752, category 3 is represented in a display area 753, category 4 is represented in a display area 754, category 5 is represented in a display area 755, category 6 is represented in a display area 756, category 7 is represented in a display area 757, category 8 is represented in a display area 758, and category 9 is represented in a display area 759.

The number of platelet cells computed for each of the established categories in process block 412 is represented by the distribution of dots 760 (only one dot labeled in FIG. 7). That is, the number of platelet cells in each established category is represented by the respective number of dots displayed in each established category (one dot per cell). Moreover, the specific location of each dot within each category indicates the values of the first and second parameters for that platelet cell in accordance with the vertical first parameter and horizontal second parameter axes.

The graphical display of the processed platelet cell data shown in cytogram 700 readily indicates one or more characteristics of the platelet cells identified and analyzed by a hematology analyzer, such as, e.g., hematology analyzer 102. For example, as shown in FIG. 7, the highest number of platelet cells appears to be in category 5 (display area 755), which may represent, e.g., normal ranges for platelet cell volume and refractive index according to the continuing example above. The graphical display of platelet analysis results in cytogram 700 may therefore be readily useful for medical diagnostic and/or research purposes.

Figure 8:
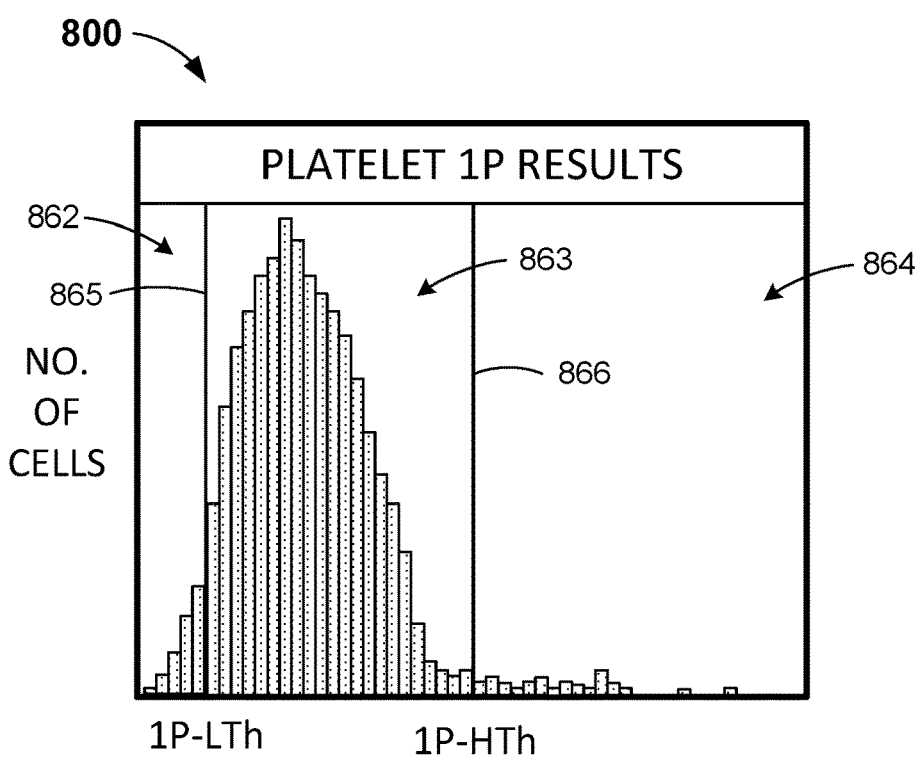
FIG. 8 illustrates an example of a histogram showing results of processed platelet cell data according to embodiments.

In some embodiments, method 400 may include displaying one or more histograms indicating the number of platelet cells in each of the high, normal, and low ranges for one of the platelet parameters. For example, FIG. 8 illustrates a histogram 800 that may be displayed on a suitable display device, such as, e.g., display device 309 of apparatus 304 in accordance with one or more embodiments. The vertical axis of histogram 800 represents the number of platelet cells, and the horizontal axis represents a first platelet parameter (1P), which may be, e.g., platelet cell volume. Histogram 800 indicates the number of platelet cells in a low range region 862, a normal range region 863, and a high range region 864 of the first parameter (1P). As shown in FIG. 8, low range region 862 extends along the horizontal axis from a predetermined lower limit (e.g., 0 fL for a volume platelet parameter) to the user-selected low threshold value 1P-LTh, represented by vertical line 865. Normal range region 863 extends along the horizontal axis from the low threshold value 1P-LTh to the user-selected high threshold value 1P-Hth, represented by vertical line 866. And high range region 864 extends along the horizontal axis from the high threshold value 1P-Hth to the predetermined upper limit of first parameter 1P, which may be, e.g., 60 fL for a volume platelet parameter. As shown in FIG. 8, histogram 800 readily indicates in which region of the first parameter a majority of platelet cells belong. This graphical display of platelet analysis results may therefore be readily useful for medical diagnostic and/or research purposes.

Figure 9:
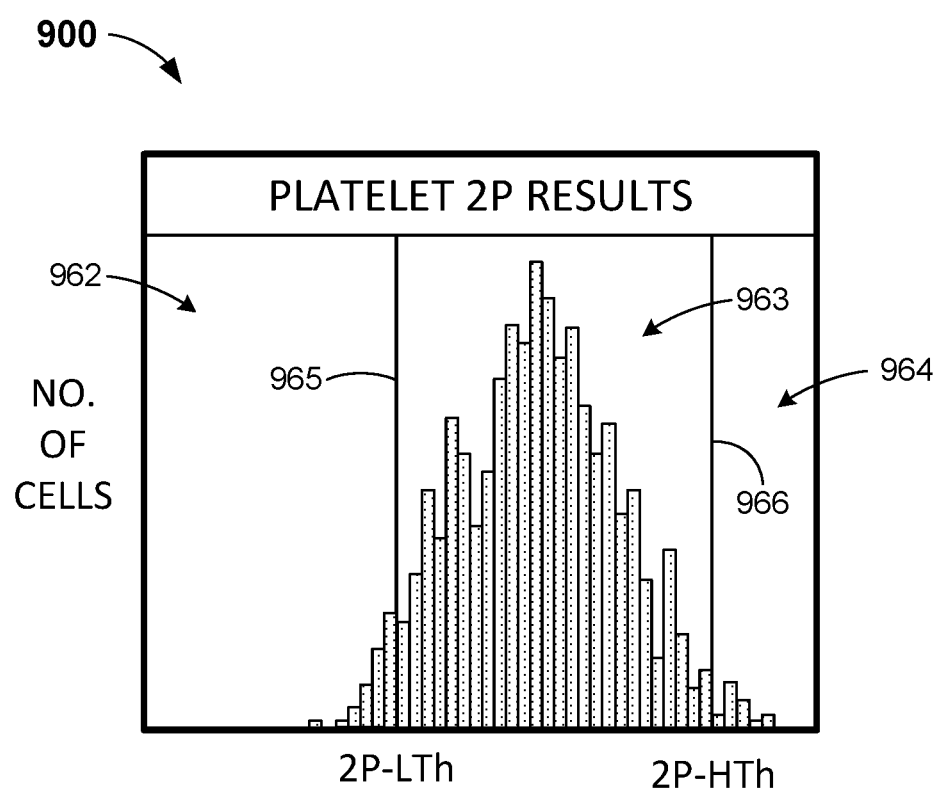
FIG. 9 illustrates an example of another histogram showing results of processed platelet cell data according to embodiments.

FIG. 9 illustrates another histogram 900 that may be displayed on a suitable display device, such as, e.g., display device 309 of apparatus 304, by method 400 in accordance with one or more embodiments. The vertical axis of histogram 900 represents the number of platelet cells, and the horizontal axis represents a second platelet parameter (2P), which may be, e.g., platelet refractive index. Histogram 900 indicates the number of platelet cells in a low range region 962, a normal range region 963, and a high range region 964 of the second parameter (2P). As shown in FIG. 9, low range region 962 extends along the horizontal axis from a predetermined lower limit (e.g., 1.3305 for a refractive index platelet parameter) to the user-selected low threshold value 2P-LTh, represented by vertical line 965. Normal range region 963 extends along the horizontal axis from the low threshold value 2P-LTh to the user-selected high threshold value 2P-Hth, represented by vertical line 966. And high range region 964 extends along the horizontal axis from the high threshold value 2P-Hth to the predetermined upper limit of the second parameter 2P, which may be, e.g., 1.4025 for a refractive index platelet parameter. As shown in FIG. 9, histogram 900 readily indicates in which region of the second parameter a majority of platelet cells belong. This graphical display of platelet analysis results may therefore be readily useful for medical diagnostic and/or research purposes.

Method 400 may further include, in some embodiments, including the platelet analysis results of table 600, cytogram 700, histogram 800, and/or histogram 900 in a data export file for use in other systems and/or apparatus.

In some embodiments, one or more process blocks of method 400 may be executed or performed in an order or sequence not limited to the order and sequence shown and described. For example, in some embodiments, process block 408 may be performed before or simultaneous with any one of process blocks 402, 404, and/or 406. Also, in some embodiments, process blocks 410 and 412 may be executed sequentially for each platelet cell processed or, alternatively, method 400 may process in process block 410 all platelet cells from the retrieved platelet cell data before proceeding to process block 412. In some embodiments, method 400 may perform process blocks 410 and 412 substantially simultaneously wherein process block 410 operates on data from one platelet cell, while process block 412 operates simultaneously on the results of another platelet cell previously processed by process block 410.

In some embodiments, a non-transitory computer-readable medium, such as, e.g., a removable storage disk or device, may include computer instructions capable of being executed in a processor and of performing all or some of method 400.

In other embodiments, computer instructions capable of being executed in a processor and of performing method 400 may be incorporated in one of more software programs of a hematology analyzer and may be executed on a processor of the hematology analyzer, which may be, e.g., hematology analyzer 102.

Persons skilled in the art should readily appreciate that the invention described herein is susceptible of broad utility and application. Many embodiments and adaptations of the invention other than those described herein, as well as many variations, modifications, and equivalent arrangements, will be apparent from or reasonably suggested by the invention and the foregoing description thereof, without departing from the substance or scope of the invention. For example, although described in connection with platelet analysis results, the apparatus and methods described herein may have application in other medical analyses wherein categorization and display of analysis results in more useful forms are desired. Accordingly, while the invention has been described herein in detail in relation to specific embodiments, it should be understood that this disclosure is only illustrative and presents examples of the invention and is made merely for purposes of providing a full and enabling disclosure of the invention. This disclosure is not intended to limit the invention to the particular apparatus, devices, assemblies, systems, or methods disclosed, but, to the contrary, the intention is to cover all modifications, equivalents, and alternatives falling within the scope of the invention, as defined by the following claims.

What is claimed is:

1. A method of processing platelet cell data stored in a memory device, the method comprising:
receiving via a processor first and second threshold values for a first parameter and third and fourth threshold values for a second parameter each entered via an input screen having a first parameter region and a second parameter region, the first parameter region displaying a predetermined minimum value and a predetermined maximum value for the first parameter, wherein the first and second threshold values are each within a range bounded by the predetermined minimum and maximum values for the first parameter;
establishing via the processor first high, first normal, and first low ranges for the first parameter and second high, second normal, and second low ranges for the second parameter in response to receiving the first, second, third, and fourth threshold values;
establishing via the processor a plurality of categories, each category based on a combination of one of the first high, first normal, and first low ranges with one of the second high, second normal, and second low ranges;
retrieving via the processor the platelet cell data from the memory device, the platelet cell data indicating a plurality of platelet cells comprising a respective plurality of first parameter values and a corresponding plurality of second parameter values, wherein each platelet cell of the plurality of platelet cells corresponds to a respective first parameter value and a respective second parameter value;
determining via the processor for each first parameter value and each corresponding second parameter value whether the first parameter value is in the first high, first normal, or first low range and whether the corresponding second parameter value is in the second high, second normal, or second low range; and
computing via the processor a number of the plurality of platelet cells in each of the plurality of categories in response to the determining.

2. The method of claim 1, wherein the first parameter comprises platelet volume, the first threshold value comprises a high platelet volume value, and the second threshold value comprises a low platelet volume value.

3. The method of claim 1, wherein the second parameter comprises platelet refractive index, the third threshold value comprises a high platelet refractive index value, and the fourth threshold value comprises a low platelet refractive index value.

4. The method of claim 1, further comprising displaying a table on a display device of the number of the plurality of platelet cells in each of the plurality of categories.

5. The method of claim 1, further comprising displaying graphically on a display device the number of the plurality of platelet cells in each of the plurality of categories.

6. The method of claim 1, further comprising displaying a cytogram or a histogram indicating the number of the plurality of platelet cells in at least one of the plurality of categories, one of the first high, first normal, and first low ranges, or one of the second high, second normal, and second low ranges.

7. The method of claim 1, further comprising:
computing a percentage of the plurality of platelet cells in each of the plurality of categories; and
displaying on a display device the number and the percentage of the plurality of platelet cells in each of the plurality of categories.

8. A non-transitory computer-readable medium comprising computer instructions that are executed in a processor to perform the method of claim 7.

9. The method of claim 1, wherein:
a first of the plurality of categories comprises a number, a percentage, or both of the plurality of platelet cells having a first parameter value in the first high range and a corresponding second parameter value in the second high range;
a second of the plurality of categories comprises a number, a percentage, or both of the plurality of platelet cells having a first parameter value in the first normal range and a corresponding second parameter value in the second high range; and
a third of the plurality of categories comprises a number, a percentage, or both of the plurality of platelet cells having a first parameter value in the first low range and a corresponding second parameter value in the second high range.

10. The method of claim 1, wherein:
a fourth of the plurality of categories comprises a number, a percentage, or both of the plurality of platelet cells having a first parameter value in the first high range and a corresponding second parameter value in the second normal range;
a fifth of the plurality of categories comprises a number, a percentage, or both of the plurality of platelet cells having a first parameter value in the first normal range and a corresponding second parameter value in the second normal range; and
a sixth of the plurality of categories comprises a number, a percentage, or both of the plurality of platelet cells having a first parameter value in the first low range and a corresponding second parameter value in the second normal range.

11. The method of claim 1, wherein:
a seventh of the plurality of categories comprises a number, a percentage, or both of the plurality of platelet cells having a first parameter value in the first high range and the corresponding second parameter value in the second low range;
an eighth of the plurality of categories comprises a number, a percentage, or both of the plurality of platelet cells having a first parameter value in the first normal range and the corresponding second parameter value in the second low range; and
a ninth of the plurality of categories comprises a number, a percentage, or both of the plurality of platelet cells having a first parameter value in the first low range and the corresponding second parameter value in the second low range.

12. A non-transitory computer-readable medium comprising computer instructions that are executed in a processor to perform the method of claim 1.

13. Apparatus for processing platelet cell data, the apparatus comprising:
a user interface comprising a user input device and a display device; and
a processor coupled to the user interface and configured to:
receive via the user interface first and second threshold values for a first parameter and third and fourth threshold values for a second parameter each entered via an input screen having a first parameter region and a second parameter region, the first parameter region displaying a predetermined minimum value and a predetermined maximum value for the first parameter, wherein the first and second threshold values are each within a range bounded by the predetermined minimum and maximum values for the first parameter;
establish first high, first normal, and first low ranges for the first parameter and second high, second normal, and second low ranges for the second parameter in response to receiving the first, second, third, and fourth threshold values;
establish a plurality of categories, each category based on a combination of one of the first high, first normal, and first low ranges with one of the second high, second normal, and second low ranges;
retrieve the platelet cell data, the platelet cell data indicating a plurality of platelet cells comprising a respective plurality of first parameter values and a corresponding plurality of second parameter values, wherein each platelet cell of the plurality of platelet cells corresponds to a respective first parameter value and a respective second parameter value;
determine for each first parameter value and each corresponding second parameter value whether the first parameter value is in the first high, first normal, or first low range and whether the corresponding second parameter value is in the second high, second normal, or second low range; and
compute a number of the plurality of platelet cells in each of the plurality of categories in response to the determining.

14. The apparatus of claim 13, wherein the apparatus is a computer or workstation comprising the user interface and the processor.

15. The apparatus of claim 14, wherein the computer is a laptop or personal computer.

16. The apparatus of claim 13, wherein the processor is configured to retrieve the platelet cell data from a memory device coupled to the processor.

17. The apparatus of claim 13, wherein the processor is configured to be coupled to a hematology analyzer, the hematology analyzer comprising a memory device storing the platelet cell data.

18. The apparatus of claim 13, wherein the processor is configured to display on the display device a table, a cytogram, or a histogram indicating the number, the percentage, or both of the plurality of platelet cells in at least one of the plurality of categories, one of the first high, first normal, and first low ranges, or one of the second high, second normal, and second low ranges.

19. The apparatus of claim 13, wherein:
- the first parameter comprises platelet volume, the first threshold value comprises a high platelet volume value, and the second threshold value comprises a low platelet volume value; and
- the second parameter comprises platelet refractive index, the third threshold value comprises a high platelet refractive index value, and the fourth threshold value comprises a low platelet refractive index value.

20. A system for processing platelet cell data, the system comprising:
- a hematology analyzer configured to analyze a sample of blood and to create the platelet cell data as a result of analyzing the blood sample, the hematology analyzer comprising a memory device and configured to store the platelet cell data in the memory device; and
- the apparatus of claim 13 coupled to the hematology analyzer.

* * * * *